United States Patent [19]

Welborn, Jr.

[11] Patent Number: 5,001,244

[45] Date of Patent: Mar. 19, 1991

[54] METALLOCENE, HYDROCARBYLALUMINUM AND HYDROCARBYLBOROXINE OLEFIN POLYMERIZATION CATALYST

[75] Inventor: Howard C. Welborn, Jr., Houston, Tex.

[73] Assignee: Exxon Chemical Patents Inc., Linden, N.J.

[21] Appl. No.: 552,397

[22] Filed: Jul. 13, 1990

Related U.S. Application Data

[63] Continuation-in-part of Ser. No. 391,222, Aug. 8, 1989, Pat. No. 4,952,714, which is a continuation-in-part of Ser. No. 210,881, Jun. 22, 1988, abandoned.

[51] Int. Cl.$^5$ .................. C07F 17/00; C07F 5/06
[52] U.S. Cl. ................. 556/53; 502/153; 502/104; 502/117; 556/7; 556/179; 556/51

[58] Field of Search ............ 556/179, 51, 52, 27, 556/53, 7; 502/152, 153, 104, 117

[56] References Cited

U.S. PATENT DOCUMENTS

| | | | |
|---|---|---|---|
| 3,049,407 | 8/1962 | Köster | 556/179 |
| 4,665,208 | 5/1987 | Welborn et al. | 556/179 |
| 4,841,004 | 6/1989 | Kaminsky et al. | 556/53 X |
| 4,874,880 | 10/1989 | Miya et al. | 556/53 |
| 4,892,851 | 1/1990 | Ewen et al. | 556/53 X |

*Primary Examiner*—Arthur C. Prescott
*Attorney, Agent, or Firm*—M. B. Kurtzman

[57] ABSTRACT

Olefin polymerization catalysts, and methods for their preparation, comprising a metallocene and the reaction product of a hydrocarbylaluminum with a trihydrocarbylboroxine. The catalyst may be homogeneous or supported.

20 Claims, No Drawings

METALLOCENE, HYDROCARBYLALUMINUM AND HYDROCARBYLBOROXINE OLEFIN POLYMERIZATION CATALYST

RELATED APPLICATIONS

This application is a continuation in part of U.S. Ser. No. 391,222 filed Aug. 8, 1989, now U.S. Pat. No. 4,952,714 which is in turn a continuation in part of U.S. Ser. No. 210,881 filed June 22, 1988, now abandoned.

BACKGROUND

1. Field of the Invention

The invention relates to a novel process for the preparation of homogeneous or heterogeneous catalysts useful in the polymerization of olefins comprising a metallocene and the reaction product of a hydrocarbylaluminum and a hydrocarbylboroxine.

2. Background of the Invention

Traditionally, ethylene and 1-olefins have been polymerized or copolymerized in the presence of hydrocarbon insoluble catalyst systems comprising a transition metal compound and an aluminum alkyl. More recently, active homogeneous catalyst systems comprising a bis(cyclopentadienyl)titanium dichloride or a bis(cyclopentadienyl)zirconium dichloride, and an alumoxane (the reaction product of an aluminum trialkyl and water) have been found to be useful for the polymerization of ethylene.

These later-developed homogeneous metallocene alumoxane catalysts represent a significant advance in the art of olefin polymerization. Advantages over the traditional Ziegler-Natta catalysts include a higher activity obtained for ethylene polymerization. Another significant advantage is that, unlike olefin polymers produced in the presence of conventional heterogeneous Ziegler catalysts, terminal unsaturation is present in polymers produced in the presence of these homogeneous catalysts.

Teachings relating to these homogeneous metallocene alumoxane catalysts include European Patent Application No. 0036242 which discloses a process for preparing ethylene and atactic propylene polymers in the presence of a halogen-free Ziegler catalyst system of (1) a cyclopentadienyl compound of the formula (cyclopentadienyl)$_n$MeY$_{4-n}$ in which n is an integer from 1 to 4, Me is a transition metal, especially zirconium, and Y is either hydrogen, a C$_1$-C$_5$ alkyl or metallo alkyl group or a radical having the following general formula: CH$_2$AlR$_2$, CH$_2$CH$_2$AlR$_2$ and CH$_2$CH(AlR$_2$)$_2$ in which R represents a C$_1$-C$_5$ alkyl or metallo alkyl group; and (2) an alumoxane. Additional teachings of homogeneous catalyst systems comprising a metallocene and alumoxane are European Patent Application No. 0069951 of Kaminsky et al., U.S. Pat. No. 4,404,344 issued Sept. 13, 1983 of Sinn et al., and U.S. application Ser. Nos. 697,308 filed Feb. 1, 1985; 501,588 filed May 27, 1983 and now U.S. Pat. No. 4,522,982; 728,111 filed Apr. 29, 1985 and 501,740 filed June 6, 1983 and now U.S. Pat. No. 4,530,914, each commonly assigned to Exxon Research and Engineering Company.

Nevertheless, these homogeneous metallocene alumoxane catalysts suffer from a disadvantage in that the ratio of alumoxane to metallocene is high, for example on the order of 1,000 to 1 or greater. Such voluminous amounts of alumoxane often requires extensive treatment of the polymer product in order to remove undesirable aluminum. A second disadvantage of the homogeneous catalyst system, which is also associated with traditional heterogeneous Ziegler catalysts, is the multiplicity of delivery systems required for introducing the individual catalyst components into the polymerization reactor.

U.S. Pat. No. 4,808,561 to Welborn, hereby incorporated by reference as if fully set forth, provides a supported metallocene alumoxane catalyst for olefin polymerization which can be usefully employed for the production of low, medium and high density polyethylenes and copolymers of ethylene with α-olefins having 3 to 18 or more carbon atoms and/or diolefins having up to 18 carbon atoms or more. The supported catalyst will polymerize olefins at commercially acceptable rates without the presence of the objectionable excess of alumoxane required in the homogeneous system. The catalyst comprises the reaction product of at least one metallocene and an alumoxane in the presence of a support material thereby providing a supported metallocene-alumoxane reaction product as the sole catalyst component.

Supported metallocene alumoxane catalysts, however, suffer a disadvantage in common with their homogeneous counterparts, namely, the method of preparation of the alumoxane component. Thus, for instance, while the '561 patent discloses that the alumoxanes can be prepared in a variety of ways, they are preferably prepared by contacting water with a solution of aluminum trialkyl, such as, for example, aluminum trimethyl, in a suitable organic solvent such as benzene or an aliphatic hydrocarbon. For example, the aluminum alkyl may be treated with water in the form of a moist solvent. In a preferred method, the aluminum alkyl, such as aluminum trimethyl, can be contacted with a hydrated salt such as hydrated copper sulfate. This method comprises treating a dilute solution of aluminum trimethyl in, for example, toluene with copper sulfate heptahydrate.

In many of these processes, because of the highly exothermic nature of the reaction between the water and the hydrocarbylaluminum, there is a high risk that the reaction can get out of control or even become explosive. While the use of CuSO$_4$.5H$_2$O as source of water allows the slow addition of water, thereby reducing the risk of local excesses of water and consequently the probability of a runaway or explosive reaction, the method suffers some disadvantages. For example, the Cu(II) may be reduced to Cu(I) or even to metallic copper during the reaction with an alkylaluminum, such as trimethylaluminum. This reduction of the copper ion can lead to the introduction of undesirable types of functionalities, such as sulfate groups or even copper, into the alumoxane preparation. Prior to using the alumoxane product as a component of a catalyst system in a polymerization process, it must therefore be filtered, purified and recrystallized. Otherwise, adverse conditions may exist during the polymerization, and the quality and quantity of the polymer may be adversely affected. Another disadvantage associated with using CuSO$_4$.5H$_2$O to prepare alumoxane is the low alumoxane yield, about 30% based on the aluminum trialkyl employed. Our copending application, U.S. Ser. No. 391,222, filed Aug. 8, 1989 and its parent U.S. Ser. No. 210,881, both hereby incorporated by reference as if fully set forth, however, teach an alternative, safer method of preparing alumoxanes.

In the preferred embodiment, a hydrocarbon soluble liquid trihydrocarbylboroxine, (RBO)$_3$, is first prepared. This can be accomplished by combining boron oxide with trihydrocarbylborane according to the following stoichiometry:

$$B_2O_3 + R'_3B \rightarrow (R'BO)_3$$

wherein R' can be a $C_1-C_{10}$ alkyl group or a $C_6-C_{10}$ aryl group, desirably a $C_1-C_4$ alkyl group and preferably R' is methyl, ethyl, propyl, butyl or mixtures thereof. Next, trihydrocarbylboroxine is combined with trialkylaluminum to form an alumoxane and trihydrocarbylborane according to the following theorized stoichiometry:

$$(n+m)(RBO)_3 + 3(n+m+1)R_3Al \rightarrow 3(RAlO)_m + 3[R-(R-Al-O)_n-AlR_2] + 3(m+n)R_3B$$

wherein the sum (m+n) is 4-80, preferably 8-80, and most preferably 10-60. The R groups of the trialkylboroxine and the trialkylaluminum can be the same or different. If the R groups are different, a mixture of alumoxane containing a mixture of R groups is produced.

Since trihydrocarbylboroxine is soluble in the hydrocarbon solution, it permits a homogeneous reaction to occur with the trialkylaluminum. This results in better control of the reaction stoichiometry and product properties, e.g., the degree of oligomerization, m and n.

There yet exists a need for a simple, safe method of preparing a metallocene-alumoxane-based catalyst effective for the polymerization of olefins that avoids the need to separately produce an alumoxane by reacting a hydrocarbyl aluminum with free water, with the hazards attendant in such reacting, or reacting a hydrocarbylaluminum with a hydrated salt capable of releasing water and subsequently processing the reaction product to remove metal ions which constitute a contaminant.

SUMMARY OF THE INVENTION

The invention provides a novel process for producing supported or unsupported catalysts, comprising a metallocene and the reaction product of a hydrocarbylaluminum and a hydrocarbylboroxine, for olefin polymerization. The process eliminates the need to react a hydrocarbylaluminum with free water or a hydrated salt in order to form an alumoxane. Consequently, the process avoids the risks inherent in these reactions. Further, the inventive process also avoids the contamination problems encountered in the use of salts, such as CuSO$_4$.5H$_2$O, to provide the water needed to form the alumoxane from the hydrocarbylaluminum. Moreover, in supported form, the inventive catalyst does not require an objectionable excess of alumoxane over metallocene.

In the inventive process, hydrocarbylaluminum is reacted with a trihydrocarbylboroxine and a metallocene to produce the unsupported metallocene alumoxane olefin polymerization catalyst. To produce a supported form of the catalyst, a hydrocarbylaluminum is combined with a trihydrocarbylboroxine and a metallocene together with a catalyst support to produce a supported alumoxane metallocene olefin polymerization catalyst.

The unsupported catalysts of the invention are especially useful in high pressure, high temperature processes for the polymerization of olefins. The supported catalyst is especially useful in gas and slurry phase olefin polymerization processes.

The metallocenes employed in the production of the catalysts are organometallic coordination compounds which are cyclopentadienyl derivatives of a Group 4b, 5b, or 6b metals of the Periodic Table (56th Edition of Handbook of Chemistry and Physics, CRC Press [1975]) and include mono, di and tricyclopentadienyls and their derivatives of the transition metals. Particularly desirable are the metallocenes of Group 4b and 5b metals such as titanium, zirconium, hafnium and vanadium.

As previously explained, the alumoxanes of the inventive catalysts are produced by the reaction of a trihydrocarbylboroxine and a hydrocarbylaluminum. The resultant alumoxanes comprise oligomeric linear and/or cyclic alumoxanes represented by the formulae:

$$R-(Al-O)_n-AlR_2$$
$$\phantom{R-(}|$$
$$\phantom{R-(Al-O)_n-}R$$

for oligomeric, linear alumoxanes and $$(-Al-O-)_m$$
$$\phantom{(-}|$$
$$\phantom{(-Al}R$$

for oligomeric, cyclic alumoxane, wherein n is 1-40, preferably 10-20, m is 3-40, preferably 3-20 and R is a $C_1-C_8$ alkyl group and preferably methyl. Generally, in the preparation of alumoxanes, a mixture of linear and cyclic compounds is obtained.

The catalyst support may be any of the solid, porous supports, such as talc, silica, silica-alumina, alumina, finely divided resinous polyolefin, and the like.

Whether in supported or unsupported form, the inventive catalysts are highly effective for use in processes for the polymerization of $C_2-C_{18}$ α-olefins. The catalysts are particularly useful for producing homopolymers of ethylene and propylene and copolymers of ethylene or propylene and higher α-olefins and/or diolefins and/or cyclic olefins such as norbornene.

DETAILED DESCRIPTION OF THE PREFERRED EMBODIMENTS

The unsupported metallocene alumoxane olefin polymerization catalyst of the invention is produced by combining a hydrocarbylaluminum with a trihydrocarbylboroxine and a metallocene. The supported metallocene alumoxane catalyst of the invention includes these constituents and, in addition, a catalyst support material.

The supported and unsupported catalyst systems of the invention are useful in the gas, liquid, or slurry phase polymerization of olefins, particularly lower α-olefins, such as ethylene, propylene, butene-1, hexene-1 and octene-1.

The polymer products are intended for fabrication into articles by extrusion, injection molding, thermoforming, rotational molding, and the like. In the polymerization process, ethylene, for example, either alone or together with α-olefins having up to about 10 carbon atoms, is contacted with the catalyst systems comprising at least one metallocene and an alumoxane.

It should be understood that the term "olefin" as used in the specification and claims encompasses not only ethylene and 1-olefins but also olefins having more than one site of unsaturation, such as diolefins, as well as cyclic olefins.

The Metallocene Component

The metallocene component of the catalyst may be any of the organometallic coordination compounds obtained as a cyclopentadienyl derivative of a transition metal. Metallocenes which are useful for preparing an active catalytic complex according to the process of this invention are the mono, bi and tri cyclopentadienyl or substituted cyclopentadienyl metal compounds and most preferably, bicyclopentadienyl compounds. The metallocenes particularly useful in this invention are represented by the general formulas:

$(Cp)_m MR_n X_q$  I wherein Cp is a cyclopentadienyl ring, M is a Group 4b or 5b transition metal and preferably a Group 4b transition metal, R is a hydrocarbyl group or hydrocarboxy group having from 1 to 20 carbon atoms, X is a halogen, and m is a whole number from 1 to 3, n is a whole number from 0 to 3, and q is a whole number from 0 to 3, and the sum of m+n+q is equal to the oxidation state of the metal;

$(C_5R'_k)_g R''_s (C_5R'_k)MQ_{3-g}$; and  II $R''_s(C_5R'_k)_2 MQ'$  III wherein $(C_5R'_k)$ is a cyclopentadienyl or substituted cyclopentadienyl; each R' is the same or different and is hydrogen or a hydrocarbyl radical such as alkyl, alkenyl, aryl, alkylaryl, or arylalkyl radicals containing from 1 to 20 carbon atoms, a silicon-containing hydrocarbyl radical, or a hydrocarbyl radical wherein two carbon atoms are joined together to form a $C_4$-$C_6$ ring; R'' is $C_1$-$C_4$ alkylene radical, a dialkyl germanium or silicon, or an alkyl phosphine or amine radical bridging two $(C_5R'_k)$ rings; Q is a hydrocarbyl radical such as aryl, alkyl, alkenyl, alkylaryl, or arylalkyl having 1-20 carbon atoms, hydrocarboxy radical having 1-20 carbon atoms or halogen and can be the same or different; Q' is an alkylidene radical having from 1 to about 20 carbon atoms, s is 0 or 1; g is 0, 1 or 2; when g is 0 or 2, s is 0; k is 4 when s is 1 and k is 5 when s is 0; and M is as defined above.

Exemplary hydrocarbyl radicals are methyl, ethyl, propyl, butyl, amyl, isoamyl, hexyl, isobutyl, heptyl, octyl, nonyl, decyl, cetyl, 2-ethylhexyl, phenyl, and the like. Exemplary alkylene radicals are methylene, ethylene, propylene, and the like. Exemplary halogen atoms include chlorine, bromine and iodine and of these halogen atoms, chlorine is preferred. Exemplary of the alkylidene radicals is methylidene, ethylidene and propylidene.

Of the metallocenes, zirconocenes, hafnocenes and titanocenes are most preferred. Illustrative but non-limiting examples of these metallocenes which can be usefully employed in accordance with this invention are monocyclopentadienyl titanocenes such as, cyclopentadienyl titanium trichloride, pentamethylcyclopentadienyl titanium trichloride, bis(cyclopentadienyl) titanium diphenyl; the carbenes represented by the formula $Cp_2Ti=CH_2$ and derivatives of this reagent such as $Cp_2Ti=CH_2 \cdot Al(CH_3)_3$, $(Cp_2TiCH_2)_2$, $Cp_2TiCH_2CH(CH_3)CH_2$, $Cp_2Ti=CHCH_2CH_2$, $Cp_2Ti=CH_2 \cdot AlR'''_2Cl$, wherein Cp is a cyclopentadienyl or substituted cyclopentadienyl radical, and R''' is an alkyl, aryl, or alkylaryl radical having from 1-18 carbon atoms; substituted bis(Cp)Ti(IV) compounds such as bis(indenyl)Ti diphenyl or dichloride, bis(methylcyclopentadienyl)Ti diphenyl or dihalides and other dihalide complexes; dialkyl, trialkyl, tetra-alkyl and penta-alkyl cyclopentadienyl titanium compounds such as bis(1,2-dimethylcyclopentadienyl)Ti diphenyl or dichloride, bis(1,2-diethylocyclopentadienyl)Ti diphenyl or dichloride and other dihalide complexes; silicon, phosphine, amine or carbon bridged cyclopentadiene complexes, such as dimethyl silyldicyclopentadienyl titanium diphenyl or dichloride, methylenedicyclopentadienyl titanium diphenyl or dichloride and other dihalide complexes and the like.

Illustrative but non-limiting examples of the zirconocenes which can be usefully employed in accordance with this invention are, cyclopentadienyl zirconium trichloride, pentamethylcyclopentadienyl zirconium trichloride, bis(cyclopentadienyl)zirconium diphenyl, bis(cyclopentadienyl)zirconium dichloride, the alkyl substituted cyclopentadienes, such as bis(ethyl cyclopentadienyl)zirconium dimethyl, bis($\beta$-phenyl-propylcyclopentadienyl)zirconium dimethyl, bis(methylcyclopentadienyl)zirconium dimethyl, and dihalide complexes of the above; di-alkyl, tri-alkyl, tetra-alkyl, and penta-alkyl cyclopentadienes, such as bis(pentamethylcyclopentadienyl)zirconium dimethyl, bis(1,2-dimethylcyclopentadienyl)zirconium dimethyl, bis(1,3-diethylcyclopentadienyl)zirconium dimethyl and dihalide complexes of the above; silicone, phosphorus, and carbon bridged cyclopentadiene complexes such as dimethylsilyldicyclopentadienyl zirconium dimethyl or dihalide, dimethylsily bridged bis(indenyl)zirconium dichloride, dimethylsilyl bridged bis(4,5,6,7-tetrahydroindenyl)zirconium dichloride, or methylphosphine dicyclopentadienyl zirconium dimethyl or dihalide, and methylene dicyclopentadienyl zirconium dimethyl or dihalide, carbenes represented by the formulae $Cp_2Zr=CH_2P(C_6H_5)_2CH_3$, and derivatives of these compounds such as $Cp_2Zr\overline{CH_2CH(CH_3)CH_2}$.

Bis(cyclopentadienyl)hafnium dichloride, bis(cyclopentadienyl)hafnium dimethyl, bis(cyclopentadienyl)vanadium dichloride, dimethylsilyl bridged bis(indenyl)hafnium dichloride, dimethylsilyl bridged bis(4,5,6,7-tetrahydroindenyl)hafnium dichloride, and the like are illustrative of other metallocenes.

Generally the use of a metallocene which comprises a bis(substituted cyclopentadienyl) zirconium will provide a catalyst complex of higher activity than a corresponding titanocene or a mono cyclopentadienyl metal compound. Hence, bis(substituted cyclopentadienyl) zirconium compounds are preferred for use as the metallocene.

The Alumoxane Component

Alumoxanes are oligomeric aluminum compounds represented by the general formula: $(R-Al-O)_m$, a cyclic compound and $R(R-Al-O-)_n AlR_2$, which is a linear compound. In the general formula, "R" is a $C_1$-$C_{10}$ alkyl group, such as methyl, ethyl, propyl, butyl, isobutyl and pentyl, and "n" is an integer from 1 to about 40 and "m" is an integer from 3 to 40, and they represent the degree of oligomerization of the alumoxane. Preferably, "R" is methyl, "n" is 4-40, and "m" is 4-40. Generally, in the preparation of alumoxanes from the reaction of a hydrocarbylaluminum and a trihydrocarbylboroxine, a mixture of linear and cyclic compounds is obtained. Generally, an alumoxane having a degree of oligomerization greater than 4 will, for a given metallocene, produce a catalyst complex of higher activity than will an alumoxane having a degree of oligomerization less than 4. In accordance with this invention the degree of oligomerization can be controlled by the ratio of boroxine to hydrocarbylaluminum. The preferred hydrocarbylaluminum species are trimethyl and triethylaluminum. The preferred hydrocarbylboroxines are trialkylboroxines and triarylboroxines, such as trimethylboroxine, triethylboroxine, tri-n-propylboroxine, tributylboroxine, and triphenylboroxine. The most preferred trihydrocarbyl boroxines are trimethylboroxine, triethylboroxine, and the unsymmetrically substituted trialkylboroxines, methyldiethylboroxine and dimethylethylboroxine.

The Catalyst Support

Typically, the support can be any of the solid, particularly, porous supports including the inorganic oxides such as silica and resinous support materials such as polyolefin. Preferably, the support material is an inorganic oxide in finely divided form.

Suitable inorganic oxide materials which are desirably employed in accordance with this invention include Group 2a, 3a, 4a or 4b metal oxides such as silica, alumina, and silica-alumina and mixtures thereof. Other inorganic oxides that may be employed either alone or in combination with silica, alumina or silica-alumina are magnesia, titania, zirconia, and the like. Other suitable support materials, however, can be employed, for example, finely divided polyolefins such as finely divided polyethylene.

The metal oxides generally contain acidic surface hydroxyl groups which will react with the alumoxane or transition metal compound. Prior to use, the inorganic oxide support is therefore dehydrated, i.e., subjected to a thermal or chemical treatment in order to remove water and reduce the concentration of the surface hydroxyl groups. The thermal treatment is carried out in vacuum or while purging with a dry inert gas such as nitrogen at a temperature of about 100° C. to about 1000° C., and preferably, from about 300° C. to about 800° C. Pressure considerations are not critical. The duration of the thermal treatment can be from about 1 to about 24 hours. However, shorter or longer times can be employed provided equilibrium is established with the surface hydroxyl groups.

Chemical dehydration can advantageously be employed as an alternative method of dehydrating the metal oxide support material. Chemical dehydration converts all water and hydroxyl groups on the oxide surface to inert species. Useful chemical agents are for example, $SiCl_4$; chlorosilanes, such as trimethylchlorosilane, dimethylaminotrimethylsilane and the like. The chemical dehydration is accomplished by slurrying the inorganic particulate material, such as, for example, silica in an inert low boiling hydrocarbon, such as, for example, hexane. During the chemical dehydration reaction, the silica should be maintained in a moisture and oxygen-free atmosphere. To the silica slurry is then added a low boiling inert hydrocarbon solution of the chemical dehydrating agent, such as, for example, dichlorodimethylsilane. The silane solution is added slowly to the silica slurry to avoid a violent reaction of the silane with water in the silica or support material. The temperature ranges during chemical dehydration reaction can be from abut 25° C. to about 120° C., however, higher and lower temperatures can be employed. Preferably, the temperature will be about 50° C. to about 70° C. The chemical dehydration procedure should be allowed to proceed until all the moisture is removed from the particulate support material, as indicated by cessation of gas or heat evolution. Normally, the chemical dehydration reaction will be allowed to proceed from about 30 minutes to about 16 hours, preferably 1 to 5 hours. Upon completion of the chemical dehydration, the solid particulate material is filtered under a nitrogen atmosphere and washed one or more times with a dry, oxygen-free inert hydrocarbon solvent. The wash solvents, as well as the diluents employed to form the slurry and the solution of chemical dehydrating agent, can be any suitable inert hydrocarbon. Illustrative of such hydrocarbons are heptane, hexane, toluene, isopentane and the like.

The specific particle size, surface area, pore volume, and number of surface hydroxyl groups characteristic of the inorganic oxide are not critical to its utility in the practice of the invention. However, since such characteristics determine the amount of inorganic oxide that it is desirable to employ in preparing the catalyst compositions, as well as affecting the properties of polymers formed with the aid of the catalyst compositions, these characteristics must frequently be taken into consideration in choosing an inorganic oxide for use in a particular aspect of the invention. For example, when the catalyst composition is to be used in a gas-phase polymerization process—a type of process in which it is known that the polymer particle size can be varied by varying the particle size of the support—the inorganic oxide used in preparing the catalyst composition should be one having a particle size that is suitable for the production of a polymer having the desired particle size. In general, optimum results are usually obtained by the use of inorganic oxides having an average particle size in the range of about 30 to 600 microns, preferably about 30 to 100 microns; a surface area of about 50 to 1,000 square meters per gram, preferably about 100 to 400 square meters per gram; and a pore volume of about 0.5 to 3.5 cc per gram, preferably about 0.5 to 2 cc per gram.

Methods for Preparing the Catalysts

The metallocene alumoxane catalysts may be prepared by several methods. The invention, however, provides a process and a catalyst wherein the alumoxane component of the catalyst is prepared by the interaction of a hydrocarbylaluminum with a trihydrocarbylboroxine.

The order of addition of metallocene, hydrocarbylaluminum, trihydrocarbylboroxine and support, if any, is not critical. When preparing a unsupported form of catalyst, it is preferred that the hydrocarbylboroxine be first added to the hydrocarbylaluminum to form the alumoxane component before addition of the metallocene. When preparing a supported form of catalyst, it is preferred to form a slurry of the support material in a suitable hydrocarbon solvent and to add the hydrocarbylaluminum first and the hydrocarbylboroxine in a second step to the slurried support before addition of the metallocene.

To prepare the hydrocarbylboroxine, boron oxide is combined with hydrocarbylborane in the molar ratio from about 2:1 to about 1:2, preferably 1:1. To prepare the alumoxane, the hydrocarbylboroxine is added to a solution of a hydrocarbylaluminum in an inert solvent. The molar ratio of hydrocarbylboroxine to hydrocarbylaluminum should be in the range from about 1:3.05 to about 1:4, preferably 1:3.3. Ratios greater than about 4 can result in an excess of unreacted hydrocarbylaluminum in the reaction product. Such excess, unreacted hydrocarbylaluminum generally will not affect the usefulness of the product hydrocarbylalumoxane. At ratios of trihydrocarbylboroxine:hydrocarbylaluminum of less than 3, alumina can be formed. These ratios may not be solely dependant upon the stoichiometry of the chemical reaction but may also depend upon other factors which influence the equilibrium of the reaction, such as temperature. Generally, the temperature of the reaction should be between about 10° C. to about 80° C. The reaction between the hydrocarbylaluminum and the hydrocarbylboroxine must be carried out in an oxygen-free, inert atmosphere which can be at atmospheric, subatmospheric, or superatmospheric pressure. Preferably the reaction is carried out at atmospheric or slightly superatmospheric pressure (1-2 bar) under nitrogen.

Completion of the reaction between the boron oxide and the hydrocarbylborane is indicated by the cessation of hydrocarbylboroxine production and the disappearance of the solid boron oxide. Generally, the reaction time will be between about 2 and about 72 hours, depending on the temperature of the reaction. The reaction time between hydrocarbylboroxine and hydrocarbylaluminum can be between about 0.1 and about 24 hours. Usually the reaction time will be between 0.5 and about 4 hours.

It is preferred that the hydrocarbylboroxine be added to the hydrocarbylaluminum. This order of mixing forces the hydrocarbylboroxine to undergo reaction in the context of a transient localized excess of hydrocarbylaluminum and a transient localized deficiency of the hydrocarbylboroxine. In order to obtain a safe reaction rate, the rate of addition of boroxine to hydrocarbylaluminum should not exceed about 0.2 moles per minute per liter of reaction medium.

The solvents employed in dissolving the hydrocarbylaluminum can be any of the known inert organic solvents, preferably aliphatic or aromatic solvents, such as toluene, benzene, hexane, heptane, iso-octane, cyclohexane, methylcyclohexane, decane, and the like. Preferably the same solvent is employed for dissolving the alkylaluminum and the boroxine. Toluene and heptane are preferred solvents. The ratio, by volume, of solvent to hydrocarbylaluminum should be at least 4:1 and preferably 8:1.

Thus, to prepare the metallocene alumoxane catalyst species, a metallocene component may be added to the solution containing the alumoxane prepared as above-described. Alternatively, the solution may be added to the metallocene component in solution. The molar ratio of the hydrocarbylaluminum used to prepare the alumoxane may usefully vary relative to the amount of metallocene added, calculated as a ratio of aluminum atom to transition metal atom, as an Al:transition metal atomic ratio of from about 1000:1 to about 1:1, but preferably from about 600:1 to about 20:1.

The supported catalyst of this invention is prepared by simply adding the reactants in a suitable solvent, preferably toluene, to a slurry of the support material in an inert organic solvent, preferably silica slurried in toluene. Although the order of addition is not critical, it is preferred to first add the hydrocarbyl aluminum to a slurry of the support material, followed by addition of the hydrocarbylboroxine, followed by the addition of the metallocene to the slurry.

The temperature maintained during the contacting of the reactants can vary widely, such as, for example, from 0° to 100° C. Greater or lesser temperatures can also be employed. Preferably, the hydrocarbylaluminum, hydrocarbylboroxine and metallocenes are added to the silica at room temperature.

The reaction between the hydrocarbylaluminum and hydrocarbylboroxine and the support material to form an alumoxane is rapid. However, the contacting of the hydrocarbylaluminum and hydrocarbylboroxine may be maintained for about one hour and up to eighteen hours or greater before addition of the metallocene. Preferably, the reaction is maintained for about one hour. The reaction of the alumoxane, the metallocene and the support material is evidenced by its exothermic nature. At all times, the individual ingredients as well as the recovered catalyst component must be protected from oxygen and moisture. Therefore, the reactions must be performed in an oxygen and moisture free atmosphere and recovered in an oxygen and moisture free atmosphere. Preferably, therefore, the reactions are performed in the presence of an inert dry gas such as, for example, nitrogen. The recovered solid catalyst is maintained in a nitrogen atmosphere.

Upon completion of the reaction of the metallocene, hydrocarbylaluminum and hydrocarbylboroxine with each other and with the support, the solid material can be recovered by any well-known technique. For example, the solid material can be recovered from the liquid by vacuum evaporation or decantation. The solid is thereafter dried under a stream of pure dry nitrogen or dried under vacuum.

The amount of alumoxane and metallocene usefully employed in preparation of the solid supported catalyst component can vary over a wide range. The concentration of the alumoxane combined with the essentially dry support can be in the range of about 0.1 to about 10 mmoles of aluminum/g of support, however, greater or lesser amounts can be usefully employed. Preferably, the alumoxane concentration will be in the range of 0.5 to 10 mmoles of aluminum/g of support and especially 1 to 5 mmoles of aluminum/g of support. The amount of metallocene added will be such as to provide an aluminum to transition metal mole ratio of from about 1:1 to about 100:1 wherein the ratio is calculated as the ratio of aluminum atom in the hydrocarbylaluminum added to the transition metal atom in the metallocene added. Preferably, the ratio is in the range from about 5:1 to about 50:1 and more preferably in the range from about 10:1 to about 20:1. These ratios are significantly less than that which is necessary for an unsupported catalyst system.

The following Example illustrates the invention and is not intended to limit the scope of the invention as described above and claimed hereafter.

Example 1—Preparation of Methylalumoxane

A 100 cc round bottom flask was equipped for magnetic stirring in an inert, dry nitrogen atmosphere. Neat trimethylaluminum (2.37 g, 0.033 moles) was weighed into the flask followed by 43 g of distilled toluene. Into another flask was weighed 1.68 g of neat triethylboroxine (0.010 moles), followed by 43 g of distilled toluene. With stirring, the triethylboroxine solution was added to the trimethylaluminum solution in 5-10 cc increments separated by 5 minute intervals. The solution remained clear and colorless during and after the additions. The solution was capped and stored under nitrogen.

Example 2—Polymerization Using Methylalumoxane

A 1-liter stainless steel reactor vessel equipped with an inclined blade stirrer, an external jacket for temperature control, a septum inlet and vent line, and a regulated supply of dry ethylene and nitrogen, was cleaned with boiling toluene and dried and deoxygenated with a nitrogen flow. The reactor temperature was adjusted to 80° C., and 400 cc of distilled toluene was added. Two milliliters of the final solution from Example 1 was injected by syringe, and the mixture was stirred at 0 psig under nitrogen. A toluene solution (0.10 cc) containing 0.10 mg of dissolved bis(n-butylcyclopentadienyl)zirconium dichloride was injected. Immediately 90 psig of ethylene was admitted and the reactor was stirred and maintained at 80° C. for 5 minutes at a constant pressure of 90 psig. The product was recovered by rapidly venting, cooling, and opening the reactor. Residual toluene was evaporated in a stream of air, and the yield was weighed. The product was determined to be 10.0 g of polyethylene by infrared and gel permeation chromatography. The catalyst activity was calculated to be 885,000 grams polymer per gram zirconium-hour-bar.

Example 3—Preparation of a Supported Catalyst

A 100 cc round bottom flask was equipped for magnetic stirring in an inert, dry nitrogen atmosphere. Ten grams of Davison 948 silica, dehydrated at 800° C. in a flowing dry nitrogen atmosphere for 5 hours, was added to the flask. A solution of 2.37 grams of neat trimethylaluminum (32.88 mmoles) and 35 cc of toluene were mixed well and then added to the dry silica all at once and the suspension was stirred at 120 rpm at 25° C. for 15 minutes. A solution of 1.68 grams of triethylboroxine (10.02 mmoles) and 10 cc of toluene was prepared and then was added to the silica trimethylaluminum-toluene slurry in 2 cc increments each 5 minutes until addition was complete. The mixture was stirred for an additional 1 hour at 25° C. Bis(n-butylcyclopentadienyl)zirconium dichloride, 270.0 mg was dissolved in 5 cc toluene and then was added all at once to the stirring mixture. The mixture was stirred for an additional 15 minutes at 25° C. after which time it was heated to 60° C. under high vacuum to remove all volatile components. The dry, free flowing supported catalyst had a light yellow color and was analyzed to contain 0.46 wt % zirconium and 6.1 wt % aluminum.

Example 4—Polymerization Using Supported Catalyst

A 1-liter stainless steel reactor vessel equipped with an inclined blade stirrer, an external jacket for temperature control, a septum inlet and vent line, and a regulated supply of dry ethylene and nitrogen, was cleaned with boiling toluene and dried and deoxygenated with a nitrogen flow. Isobutane (450 cc) and 50 cc of 1-butene were added to the reactor at 20° C. from a calibrated burette. The reactor contents were stirred at 1250 rpm and heated to 65° C. The reactor pressure was increased to 300 psig by adding purified ethylene. A stainless steel, solid catalyst addition tube was loaded with 100 mg of the dry catalyst prepared in Example 3. The catalyst was pressured into the reactor with 420 psig of ethylene and ethylene was supplied to the reactor on pressure demand at 420 psig for 15 minutes while maintaining the temperature at 65° C. The ethylene-1-butene copolymer (20 grams) was recovered as a free-flowing, granular product by rapidly venting and opening the reactor. After drying in air the weight average molecular weight of the product was determined to be 200,000 and the polydispersity was 2.0.

Example 5—Preparation of a Unsupported Catalyst

A 25 liter vessel with an internal paddle stirrer (120 rpm) was used in the preparation of this catalyst. The vessel was maintained under a positive pressure of purified nitrogen and at 25° C. during all stages of the preparation of this catalyst. The empty, clean vessel was first charged with a 10.0 liters of dry toluene. A heptane solution of trimethylaluminum (0.62 liters of 5 wt % trimethylaluminum in heptane, containing 0.31 moles of trimethylaluminum) was added to the vessel and the solution was mixed for 5 minutes. A solution of 18.4 cc of triethylboroxine (0.10 moles) was prepared in 500 cc of heptane. The triethylboroxine solution was then added in three equal portions (approximately 165 cc) to the stirring toluene-trimethyl-aluminum solution over a 10 minute period. Thereafter, 4.19 grams of bis(n-butylcyclopentadienyl)zirconium dichloride was added and the solution was stirred for 15 minutes. This catalyst solution was used in the following example.

Example 6—Polymerization at High Pressure

In this Example a stirred 1000 cc steel autoclave reaction vessel which was equipped to perform continuous Ziegler polymerization reactions at pressures up to 2500 bar and temperatures up to 300° C. was used. The reaction system was supplied with a thermocouple and pressure transducer to measure temperature and pressure continuously, and with means to supply continuously purified compressed ethylene, hydrogen, and 1-butene. Equipment for continuously introducing a measured flow of catalyst solution and equipment for rapidly venting and quenching the reaction and of collecting the polymer product were also a part of the reaction system. In this Example, the polymerization was performed with a molar ratio of ethylene to 1-butene of 1.6 without the addition of a solvent. In this Example, the temperature of the cleaned reactor containing ethylene and 1-butene was equilibrated at the desired reaction temperature of 180° C. The catalyst solution prepared in Example 5 was continuously fed by a high pressure pump into the reactor at a rate of 600 cc/hour which resulted in a temperature of 180° C. in the reactor. During this run, ethylene and 1-butene were pressured into the autoclave at a total pressure of 1300 bar at a mass flow rate of 50 kg/hour. The reactor contents were stirred at 1000 rpm. The yield of polymer product was 2.9 kg/hour of an ethylene-1-butene copolymer which had weight average molecular weight of 36,110, a polydispersity of 2.2 and a density of 0.9275 g/cc.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed:

1. A method of preparing a metallocene containing catalyst effective for olefin polymerization, comprising:

(a) reacting a hydrocarbylaluminum with a hydrocarbylboroxine; and (b) adding to the reaction product at least one metallocene of the Group 4b, 5b or 6b metals.

2. The method of claim 1 wherein the hydrocarbylaluminum and the hydrocarbylboroxine are reacted in a molar ratio hydrocarbylaluminum:hydro-carbylboroxine of from about 3:1 to about 4:1.

3. The method of claim 1 wherein the metallocene is added in an amount to provide an atomic ratio of transition metal:aluminum of from about 1:600 to about 1:20.

4. The method of claim 1 wherein the metallocene is a zirconocene, hafnocene or a titanocene.

5. The method of claim 2 wherein the metallocene is a zirconocene or hafnocene.

6. A method of preparing a supported catalyst comprising the reaction product of at least one metallocene, a hydrocarbylaluminum and a hydrocarbylboroxine, effective for olefin polymerization comprising:

combining a hydrocarbylaluminum with a hydrocarbylboroxine and at least one metallocene of the Group 4b, 5b or 6b transition metals, in the presence of a catalyst support material, in an amount sufficient to provide from about 0.1 to about 10 millimoles of aluminum per gram of support.

7. The method of claim 6 wherein the hydrocarbylaluminum and hydrocarbylboroxine are combined in a molar ratio hydrocarbylaluminum:hydrocarbylboroxine of from about 3:1 to about 4:1.

8. The method of claim 6 wherein the atomic ratio of transition metal:aluminum contacted is from about 1:600 to about 1:1.

9. The method of claim 6 wherein the metallocene is a zirconocene, hafnocene or a titanocene.

10. The method of claim 6 wherein the degree of oligomerization of the alumoxane product of the reaction of the hydrocarbylaluminum and the hydrocarbylboroxine is from about 2 to about 40.

11. The method of claim 10 wherein the metallocene is a zirconocene or hafnocene.

12. The method of claim 6 wherein the catalyst support is a Group 2a, 3a, 4a, 4b metal oxide, or finely-divided polyolefinic material.

13. The method of claim 11 wherein the catalyst support is a Group 2a, 2a, 4a, 4b metal oxide, or finely-divided polyolefinic material.

14. An olefin polymerization catalyst comprising the reaction product of (a) at least one metallocene of the Group 4b, 5b or 6b transition metals; and (b) the reaction product of a hydrocarbylaluminum with a hydrocarbylboroxine.

15. The catalyst of claim 14 wherein the atomic ratio of aluminum to transition metal is from about 600:1 to about 1:1.

16. The catalyst of claim 14 wherein the metallocene is a zirconocene, a hafnocene or a titanocene, or mixtures thereof.

17. The catalyst of claim 14 further comprising a catalyst support comprising a Group 2a, 3a, 4a, 4b metal oxide or finely-divided polyolefinic material.

18. The catalyst of claim 17 wherein the atomic ratio of aluminum:transition metal is from about 100:1 to about 1:1.

19. The catalyst of claim 17 wherein the metallocene is a zirconocene, hafnocene or a titanocene.

20. A process for the polymerization of olefins comprising contacting olefins with the catalyst of claims 14 or 17 to produce a polymeric product.

* * * * *